United States Patent [19]

Philipp et al.

[11] 4,420,476

[45] Dec. 13, 1983

[54] BENZOFURO[3,2-C]PYRAZOL-3-AMINE DERIVATIVES

[75] Inventors: Adolf Philipp, St. Laurent; Ivo Jirkovsky, Montreal; René Martel, Candiac, all of Canada

[73] Assignee: Averst McKenna & Harrison, Inc., Montreal, Canada

[21] Appl. No.: 380,973

[22] Filed: May 24, 1982

[51] Int. Cl.³ .................. A61K 31/62; A61K 31/485; A61K 31/415; A61K 31/44; C07D 491/44

[52] U.S. Cl. .................. 424/232; 548/359; 548/370; 546/271; 424/260; 424/263; 424/273 P; 549/466

[58] Field of Search .................. 548/359, 370; 424/273 P; 546/271; 424/263, 232, 260

[56] References Cited

U.S. PATENT DOCUMENTS 4,140,785  2/1979  Hoffman et al. ............... 424/273 P

OTHER PUBLICATIONS

K. N. Wadodkar et al., Indian J. Chem., 12, 224 (1974).
W. U. Malik et al., Indian J. Chem., 9, 655 (1971).
W. J. Barry et al., J. Chem. Soc., 4974 (1956).
S. B. Awad et al., Aust. J. Chem., 28, 601 (1975).
K. E. Chippendale et al., J. Chem. Soc., Perkin Trans. I, 129 (1973).
F. Sauter et al., Monatsh. Chem., 105, 869 (1974).
D. N. Reinhoudt and C. G. Kouwenhoven, Rec. Trav. Chim. Pays-Bas, 93, 321 (1974).
Le Quoc Khanh and B. Laude, C. R. Acad. Sci., Ser. C, 276, 109 (1973).
W. A. Mosher et al., J. Org. Chem., 37, 2402 (1972).

*Primary Examiner*—Richard Raymond
*Assistant Examiner*—Natalia Harkaway
*Attorney, Agent, or Firm*—Arthur E. Wilfond

[57] ABSTRACT

Herein is disclosed benzofuro[3,2-c]pyrazol-3-amine derivatives, therapeutically acceptable acid addition salts thereof, processes for their preparation, methods of using the derivatives and pharmaceutical compositions. The derivatives are useful for producing analgesia in a mammal. In addition, some of the derivatives are useful for inhibiting gastric acid secretion, convulsions, anxiety and aggression, and producing muscle relaxation, hypnosis and sedation in a mammal.

30 Claims, No Drawings

BENZOFURO[3,2-C]PYRAZOL-3-AMINE DERIVATIVES

RELATED APPLICATIONS

Related hereto are U.S. Patent Application Ser. No. 380,974 and U.S. Patent Application Ser. No. 380,972, both filed on the same date as this application.

BACKGROUND OF THE INVENTION

This invention relates to novel benzofuro[3,2-c]pyrazol-3-amine derivatives, to therapeutically acceptable acid addition salts thereof, to processes for their preparation, to methods of using the derivatives, and to pharmaceutical compositions of the derivatives. These derivatives are useful for producing analgesia in a mammal without objectionable side effects of the narcotic analgesic agents. Furthermore, the derivatives produce useful analgesia at doses, which do exhibit neither antiinflammatory nor paralytic effects. In addition, some of the derivatives are useful for inhibiting convulsions, anxiety and aggression, for producing muscle relaxation and hypnosis, and for inhibiting gastric acid secretion in a mammal.

A number of benzofuro[3,2-c]pyrazole are known and described, for example, D. N. Reinhoudt and C. G. Kouwenhove, Rec. Trav. Chim. Pays-Bas, 93, 321 (1974); Le Quoc Khanh and B. Laude, C. R. Acad. Sci., Ser. C, 276, 109 (1973); W. A. Mosher et al., J. Org. Chem., 37, 2402 (1972); K. N. Wadodkar et al., Indian J. Chem., 12, 224 (1974); and W. U. Malik et al., Indian J. Chem., 9, 655 (1971). A number of benzothieno(3,2-c)pyrazol derivatives are also known, for example, W. J. Barry et al., J. Chem. Soc., 4974 (1956); S. B. Awad et al., Aust. J. Chem., 28, 601 (1975); K. E. Chippendale et al., J. Chem. Soc., Perkin Trans. I, 129 (1973); and F. Sauter et al., Monatsh. Chem., 105, 869 (1974). The compounds reported in the above references lack the substituents on the benzofuro[3,2-c]pyrazole ring system which are characteristic of the compounds of this invention. A number of 1H-benzothieno[3,2-c]pyrazol-3-amines are disclosed by H. E. Hoffman et al., U.S. Pat. No. 4,140,785, issued Feb. 20, 1979. The latter amines are readily differentiated from the compounds thereof by having a sulfur atom in the ring system and by having as their sole use chemical intermediates for preparing compounds useful in the treatment of diseases caused by rhinoviruses.

SUMMARY OF THE INVENTION

The compounds of this invention are represented by formula I

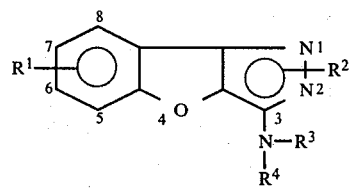

in which $R^1$ is hydrogen, halogen, lower alkyl, lower alkoxy, hydroxy or trifluoromethyl; $R^2$ represents one lower alkyl substituent on either of the adjacent nitrogen atoms; $R^3$ is hydrogen, lower alkyl, trihalomethyl(lower)alkyl; oxo(lower)alkyl; lower alkanoyl; 2-, 3- or 4-pyridinyl(lower)alkyl; lower alkylaminocarbonyl or lower alkylaminothiocarbonyl; and $R^4$ is hydrogen or lower alkyl; or a therapeutically acceptable acid addition salt thereof.

The above compounds of formula I include the compounds of formulae Ia and Ib

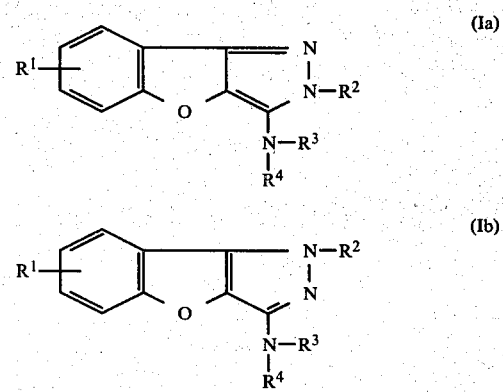

in which $R^1$, $R^2$, $R^3$ and $R^4$ are as defined herein.

A preferred group of compounds of this invention is represented by formula I in which $R^1$ is hydrogen, halogen, lower alkyl, lower alkoxy or trifluoromethyl; $R^2$ represents one lower alkyl substituent on either of the adjacent nitrogen atoms; $R^3$ is hydrogen, lower alkyl, trifluoromethyl(lower)alkyl, oxo(lower)alkyl or 2-pyridinyl(lower)alkyl; and $R^4$ is hydrogen or lower alkyl, or a therapeutically acceptable acid addition salt thereof.

Another preferred group of compounds of this invention is represented by formula Ia in which $R^1$ is hydrogen, halogen, lower alkyl, lower alkoxy or trifluoromethyl; $R^2$ is lower alkyl; $R^3$ is hydrogen, lower alkyl, trifluoromethyl(lower)alkyl, or oxo(lower)alkyl; and $R^4$ is hydrogen or lower alkyl, or a therapeutically acceptable acid addition salt thereof.

A most preferred group of compounds of this invention is represented by formula Ia in which $R^1$ is hydrogen, bromo, chloro or lower alkyl; $R^2$ is methyl; $R^3$ is hydrogen, lower alkyl, trifluoromethyl(lower)alkyl or oxo(lower)akyl; and $R^4$ is hydrogen, or a therapeutically acceptable acid addition salt thereof.

A pharmaceutical composition is provided by admixing the compound of formula I, or a therapeutically acceptable acid addition salt thereof, with a pharmaceutically acceptable carrier.

The compounds of this invention are used to produce analgesia in a mammal by administering to the mammal an effective analgesic amount of a compound of formula I or a therapeutically acceptable acid addition salt thereof.

The compounds of formula I or a therapeutically acceptable acid addition salt thereof can be prepared by selecting a process from the group of:

(a) cyclodehydrating a hydrazide of formula II

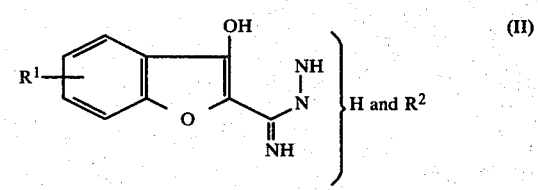

in which $R^1$ is as defined herein and $R^2$ is a lower alkyl group on one of the nitrogen atoms of the hydrazide to obtain the corresponding compound of formula I in which $R^1$ and $R^2$ are as defined herein, and $R^3$ and $R^4$ are hydrogen;

(b) cyclodehydrating a hydrazide of formula IIa

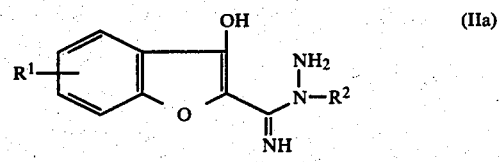

in which $R^1$ and $R^2$ are as defined herein to obtain the corresponding compound of formula Ia in which $R^1$ and $R^2$ are as defined herein, and $R^3$ and $R^4$ are hydrogen;

(c) cyclodehydrating a hydrazide of formula IIb

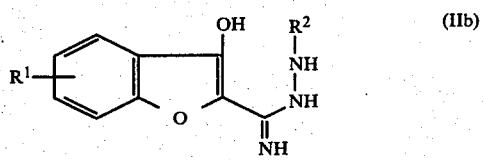

in which $R^1$ and $R^2$ are as defined herein to obtain the corresponding compound of formula Ib in which $R^1$ and $R^2$ are as defined herein, and $R^3$ and $R^4$ are hydrogen;

(d) subjecting the compound of formula I in which $R^1$ and $R^2$ are as defined herein, and $R^3$ and $R^4$ are hydrogen to acylation, reduction, alkylation, or to reaction with methyl isocyanate or methyl isothiocyanate, in optional order and to the extent required to obtain the corresponding compound of formula I in which $R^1$ and $R^2$ are as defined herein; $R^3$ is lower alkyl; trihalomethyl(lower)alkyl; oxo(lower)alkyl; lower alkanoyl; lower alkylaminocarbonyl; 2-, 3- or 4-pyridinyl(lower)alkyl, or lower alkylaminothiocarbonyl; and $R^4$ is hydrogen or lower alkyl; and (e) reacting a compound of formula I in which $R^1$, $R^2$, $R^3$ and $R^4$ are as defined herein with a therapeutically acceptable acid to obtain the corresponding compound of formula I as the salt with a therapeutically acceptable acid.

Formula II represents the combination of formulae IIa and IIb. In formula II, the group $R^2$ is attached to either of the two nitrogen atoms of the hydrazide function and hydrogen to the other.

DETAILED DESCRIPTION OF THE INVENTION

The term "lower alkyl" as used herein means straight and branched chain alkyl radicals containing from one to six carbon atoms, preferably one to three carbon atoms, and includes, methyl, ethyl, propyl, 1-methylethyl, butyl, 1,1-dimethylethyl and pentyl, unless stated otherwise.

The term "halo" as used herein means halo radicals and includes fluoro, chloro, bromo and iodo, unless stated otherwise.

The term "lower alkoxy" as used herein means straight chain alkoxy radicals containing from one to six carbon atoms and branched chain alkoxy radicals containing three or four carbon atoms and includes methoxy, ethoxy, 1-methylethoxy, butoxy, hexoxy and the like.

The term "lower alkanoyl" as used herein means straight chain 1-oxoalkyl radicals containing from two to six carbon atoms and branched chain 1-oxoalkyl radicals containing four to six carbon atoms and includes acetyl, 1-oxopropyl, 2-methyl-1-oxopropyl, 1-oxohexyl and the like.

The term "oxo(lower)alkyl" as used herein means straight chain oxoalkyl radicals containing from two to six carbon atoms and branched chain oxoalkyl radicals containing four to six carbon atoms wherein the oxo function is located at a carbon atom other than position 1 of the lower alkyl chain, and includes 2-oxoethyl, 3-oxobutyl, 2-ethyl-3-oxobutyl and the like.

The term "lower alkanol" as used herein means both straight and branched chain alkanols containing from one to four carbon atoms and includes methanol, ethanol, isopropanol, butanol and the like.

The term "lower alkanoic acid" as used herein means both straight and branched chain alkanoic acids containing from one to six carbon atoms and includes formic acid, acetic acid, propanoic acid, 3-methylbutanoic acid and the like.

The term "organic proton acceptor" as used herein means the organic bases or amines, for instance, triethylamine, pyridine, N-ethylmorpholine and 1,5-diazabicyclo[4.3.0]non-5-ene.

The term "inorganic proton acceptor" as used herein means the inorganic bases, preferably the alkali methyl hydroxides, carbonates and bicarbonates, for example, sodium hydroxide, potassium hydroxide, sodium carbonate, sodium bicarbonate and potassium carbonate.

The term "proton acceptor" as used herein means a proton acceptor selected from an organic proton acceptor and inorganic proton acceptor, as defined hereinabove.

The term "complex metal hydride" as used herein means metal hydride reducing agents and includes, for example, lithium aluminum hydride, lithium aluminum hydride-aluminum chloride, aluminum hydride-aluminum chloride, diborane, diisobutylaluminum hydride, borane methyl sulfide and sodium borohydride-aluminum chloride.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids, the organic acids, e.g., formic, acetic, maleic, methanesulfonic, malic, citric, or tartaric acid; and acids which are sparingly soluble in body fluids and which impart slow-release properties to their respective salts, e.g., pamoic acid, tannic acid or carboxymethyl cellulose. The additions salts thus obtained are the functional equivalent of the parent base compound in respect to their therapeutic use. Hence, these addition salts are included within the scope of this invention and are limited only by the requirement that the acids employed in forming the salts be therapeutically acceptable.

The novel compounds of formula I exhibit useful biological activites in several pharmacological tests. The compounds of formula I exert valuable analgesic effects in a mammal. Furthermore, some of the compounds of formula I are useful for inhibiting convulsions, anxiety and aggression, for producing muscle relaxation and hypnosis, and for inhibiting gastric acid secretion in a mammal.

The analgesic activity of the compounds of formula I or their acid addition salts with therapeutically acceptable acids can be demonstrated in standard pharmacologic tests such as, for example, the test described by S. Ankier, European Journal of Pharmacology, 27, 1 (1974). In this test for analgesia, the hot plate apparatus (Analgesia Meter Model 475, Technilab Instruments, Inc., Pequannock, N.J., United States) was heated to a temperature of 55° C. Male albino mice weighing 18–23 g were used. The control vehicle and compound were each administered intraperitoneally to separate groups of 10 mice which were then tested at durations of 20 min and 40 min from the time of injection. For each control testing, the average reaction time (amount of time elapsed until the mouse shook or licked a hindpaw) was calculated and multiplied by 1.5. This figure was designated as the "analgesic value" or A.V. A maximum cut-off time of 60 sec. was used to avoid tissue damage. A mouse whose reaction time equalled or exceeded this value was considered analgesic. From these values an $ED_{50}$ was calculated.

Using the above method, the compounds of formula I exhibit analgesic effects in mice at an i.p. dose in the range from about 10 to 250 mg per kg of body weight. For example, the following representative compounds are effective analgesic agents when administered intraperitoneally to the mouse (the effective i.p. dose to obtain the $ED_{50}$ in mg per kg of body weight is given in the parentheses): 6-chloro-2-methyl-2H-benzofuro[3,2-c]pyrazol-3-amine (described in Example 6, 122 mg/kg), 2-methyl-2H-benzofuro[3,2-c]pyrazol-3-amine hydrochloride (described in Example 6, 81 mg/kg), 7-chloro-2-methyl-2H-benzofuro[3,2-c]pyrazol-3-amine (described in Example 6, 200 mg/kg), 7-bromo-2-methyl-2H-benzofuro[3,2-c]pyrazol-3-amine (described in Example 6, 137 mg/kg), 2,5-dimethyl-2H-benzofuro[3,2-c]pyrazol-3-amine (described in Example 6, 56 mg/kg), 2,7-dimethyl-2H-benzofuro[3,2-c]pyrazol-3-amine (described in Example 6, 129 mg/kg), N-(2,2,2-trifluroethyl)-2-methyl-2H-benzofuro[3,2-c]pyrazol-3-amine (described in Example 8, 95 mg/kg), and 4-[(2-methyl-2H-benzofuro[3,2-c]pyrazol-3-yl)amino]-2-butanone (described in Example 12, 96 mg/kg).

In addition, the anticonvulsant activity of most of the compounds of formula I or a therapeutically acceptable acid addition salt thereof can be shown by using the test described by E. A. Swinyard et al., J. Pharmacol. Exp. Ther., 106, 319 (1952) for the inhibition of maximal electroshock. In this test for anticonvulsant activity, electroconvulsions were produced using corneal electrodes and alternating current of supramaximal intensity (30 mA, 0.2 sec.). Groups of 10 mice were injected with the test compound i.p., or the vehicle 60 min before being subjected to electroshock. The results are expressed as the percent of mice protected from the hind limb tonic extensor component.

Using the latter method, the compounds of formula I exhibit anticonvulsant activity in mice at an i.p. dose in the range from about 30 to about 500 mg per kg of body weight. For example, the following representative compounds are effective anticonvulsant agents when administered intraperitoneally to the mouse (the effective i.p. dose to obtain the $ED_{50}$ in mg per kg of body weight is given in the parentheses): 6-chloro-2-methyl-2H-benzofuro[3,2-c]pyrazol-3-amine (described in Example 6, 103 mg/kg), 2-methyl-2H-benzofuro[3,2-c]pyrazol-3-amine hydrochloride (described in Example 6, 115 mg/kg), 7-chloro-2-methyl-2H-benzofuro[3,2-c]pyrazol-3-amine (described in Example 6, 60 mg/kg), 7-bromo-2-methyl-2H-benzofuro[3,2-c]pyrazol-3-amine (described in Example 6, 50 mg/kg), 2,5-dimethyl-2H-benzofuro[3,2-c]pyrazol-3-amine (described in Example 6, 58 mg/kg), 5-methoxy-2-ethyl-2H-benzofuro[3,2-c]pyrazol-3-amine (described in Example 6, 165 mg/kg), 7-bromo-N-butyl-2-methyl-2H-benzofuro[3,2-c]pyrazol-3-amine (described in Example 7, 130 mg/kg), N-(2,2,2-trifluoroethyl)-2-methyl-2H-benzofuro[3,2-c]pyrazol-3-amine (described in Example 8, 80 mg/kg) and 4-[(2-methyl-2H-benzofuro[3,2-c]pyrazol-3-yl)amino]-2-butanone (described in Example 12, 63 mg/kg).

The compounds of formula I of this invention are used alone or in combination with pharmacologically acceptable carriers, the proportion of which is determined by the solubility and chemical nature of the compound, chosen route of administration and standard biological practice. For example, they are administered orally in solid form, i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as analgesic agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective analgesic amount of the compounds for i.p. administration usually ranges from about 10 to about 250 mg per kilogram body weight per day in single or divided doses although, as aforementioned, variations will occur. However a dosage level that is in the range of from about 25 to about 150 mg per kilogram body weight per day in single or divided doses is employed most desirably for i.p. administration in order to achieve effective results. For oral administration, effective amounts can range from about 25 to about 500 mg per kilogram body weight per day in single or divided doses preferably about 40 to 400 mg per kilogram of body weight per day.

A compound of formula I or a therapeutically acceptable acid addition salt thereof can also be used to produce beneficial analgesic effects when combined with a therapeutically effective amount of an agent used for analgesia. The combination produces an analgesic effect which is either additive of the individual agents or greater than each individual agent alone. Such analgesic agents include, for example, acetylsalicyclic acid, acetaminophen, etodolac, aminopyrine, codeine, morphine, and the like. Suitable methods of administration, compositions and dosages of the agents are well known in the art; for instance, see "Physicians' Desk Reference", 36th ed., Medical Economics Co., Oradell, N.J., United States, 1982 and "AMA Drug Evaluations", 3rd ed., PSG Publishing Company, Inc., Littleton, Mass., U.S.A., 1977. When used in combination, a compound of formula I or its therapeutically acceptable acid addition salt is administered as described previously; however a lower dose can be used for efficacious results.

A noteworthy feature of the compounds of formula I is that they are effective analgesic agents at doses which do not elicit paralytic effects. For example, 1-methyl-1H-benzofuro[3,2-c]pyrazol-3-amine hydrochloride exhibits effective analgesic properties in mice at oral doses ranging from 30 to 100 mg/kg whereas paralyzing effects in the same species are not observed even when oral doses of the compound are given up to 1000 mg/kg.

The compounds of formula I are prepared in the following manner.

The following reaction scheme, wherein $R^1$ and $R^2$ are as defined herein, illustrates a method for preparing the intermediates of formula IIa and IIb.

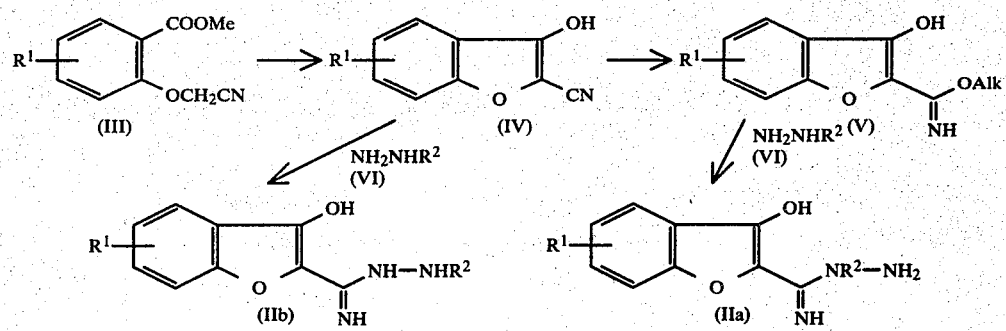

Many of the acetonitriles of formula III are described in the chemical literature, e.g. R. Bryant et al., J. Chem. Soc., 2361 (1965), or can be prepared by reacting the appropriate methyl 2-hydroxybenzoate with chloroacetonitrile.

Cyclization of the acetonitrile of formula III, with sodium methoxide in an inert solvent, affords the corresponding carbonitrile of formula IV in which $R^1$ is as defined herein. Some of the carbonitriles of formula IV are known, for example, R. Bryant et al., cited above.

The carbonitrile of formula IV is readily converted into the corresponding carboximidate of formula V in which $R^1$ is as defined herein and Alk is lower alkyl having one to four carbon atoms by reacting the carbonitrile with a lower alkanol in the presence of dry hydrogen chloride at 0° to 50° C. for 0.5 to 10 hours and isolating the carboximidate of formula V as the hydrochloride salt.

Reaction of the carboximidate of formula V with about one to five molar equivalents of a hydrazine of formula VI in which $R^2$ is as defined herein in an inert solvent gives the corresponding hydrazide of formula IIa in which $R^1$ and $R^2$ are as defined herein. A preferred solvent for the reaction is benzene or acetonitrile and the reaction is conducted preferably at about 20° to 100° C. for about one hour to three days.

In a similar reaction, the compound of formula IV is condensed with about one to five molar equivalents of a hydrazine of formula VI in an inert solvent to obtain the corresponding hydrazide of formula IIb in which $R^1$ and $R^2$ are as defined herein. Benzene is the preferred inert solvent and the reaction is conducted preferably at about 50° to 100° C. for 0.5 to 10 hours. In some instances, the condensation of the compound of formula V with the hydrazide of formula VI gives a mixture of the compounds of formulae IIa and IIb. From this mixture, either of the compounds of formula IIa or IIb can be separated by standard methods, e.g. crystallization or chromatography.

Formula II represents the combination of formulae IIa and IIb. In formula II, the group $R^2$ is attached to either of the two nitrogen atoms of the hydrazide function and hydrogen to the other.

Cyclodehydration of the hydrazide of formula II with a dehydrating agent gives the corresponding compound of formula I in which $R^1$ and $R^2$ are as defined herein, and $R^3$ and $R^4$ are hydrogen. Accordingly, the hydrazide of formula IIa gives the corresponding compound of formula Ia and the hydrazide of formula IIb gives the corresponding compound of formula Ib. The cyclodehydration is best performed by using an excess of a dehydrating agent, for example, polyphosphoric acid, trifluoroacetic acid and phosphorus oxychloride. Polyphosphoric acid is the preferred dehydrating agent. Usually, the cyclodehydration is conducted at about 50° to 125° C. for about two to 15 hours.

If desired, the compounds of formula I, prepared as described above, can be converted to other compounds of formula I.

In one conversion, the compound of formula I in which $R^1$ and $R^2$ are as defined herein, and $R^3$ and $R^4$ are hydrogen is acylated to obtain the corresponding compound of formula I in which $R^1$ and $R^2$ are as defined herein, $R^3$ is lower alkanoyl, and $R^4$ is hydrogen. Any of the usual methods of acylation can be used. For example, reaction with about one to five molar equivalents of a lower alkanoyl chloride or bromide in the presence of a proton acceptor in an inert organic solvent at about 0° to 50° C. for one to ten hours affords the corresponding compound of formula I in which $R^3$ is lower alkanoyl and $R^4$ is hydrogen. In another acylation method, reaction of the compound of formula I in which $R^1$ and $R^2$ are as defined herein, and $R^3$ and $R^4$ are hydrogen with about one to ten molar equivalents of an anhydride of a lower alkanoic acid at 0° to 50° C. for one to ten hours gives the corresponding compound of formula I in which $R^3$ is lower alkanoyl and $R^4$ is hydrogen. In the latter method, the anhydride can act as the solvent or an inert organic solvent can be used.

Reduction of the latter compound of formula I in which $R^3$ is lower alkanoyl gives the corresponding compound of formula I in which $R^1$ and $R^2$ are as defined herein, $R^3$ is a lower alkyl having a methylene group adjacent the nitrogen, and $R^4$ is hydrogen. The reduction is best performed with an excess of a complex metal hydride, for example, diborane, lithium aluminum hydride or diisobutylaluminum hydride. A preferred method of reduction uses about three to ten molar equivalents of diborane, as reducing agent, in an inert organic solvent, preferably tetrahydrofuran, at 50° to 100° C. for about one to ten hours.

The combination of the last two steps, i.e. acylation and reduction has the effect of alkylating the compound of formula I, in which $R^1$ and $R^2$ are as defined herein, and $R^3$ and $R^4$ are hydrogen, to give the corresponding compound of formula I in which $R^3$ is lower alkyl.

Another alkylation involves the reaction of the compound of formula I in which $R^1$ and $R^2$ are as defined herein, and $R^3$ and $R^4$ are hydrogen with about one molar equivalent of a lower alkyl bromide, chloride or iodide in the presence of an inorganic or organic proton acceptor in an inert organic solvent to give the corresponding compound of formula I in which $R^1$ and $R^2$ are as defined herein, $R^3$ is lower alkyl and $R^4$ is hydrogen. This alkylation usually is performed at 5° to 50° C. for one to ten hours.

The compounds of formula I in which $R^1$ and $R^2$ are as defined herein, $R^3$ is oxo(lower)alkyl and $R^4$ is hydrogen can be prepared by alkylating the corresponding compound of formula I in which $R^1$ and $R^2$ are as defined herein, and $R^3$ and $R^4$ are hydrogen with about one molar equivalent of an oxo(lower)alkyl bromide, chloride or iodide in the same manner as described in the latter alkylation. Other methods are also available for preparing some of the compounds of formula I in which $R^3$ is oxo(lower)alkyl. For example, a preferred method of preparing the compounds of formula I in which $R^1$ and $R^2$ are as defined herein, $R^3$ is 3-oxobutyl and $R^4$ is hydrogen involves the reaction of the corresponding compound of formula I in which $R^3$ and $R^4$ are hydrogen with methyl vinyl ketones; generally, one to five molar equivalents of methyl vinyl ketone is employed in an inert organic solvent at about 10° to 40° C. for about 10 to 30 hours.

Compounds of formula I in which $R^1$ and $R^2$ are as defined herein, $R^3$ is trihalomethyl(lower)alkyl, and $R^4$ is hydrogen can be prepared by alkylating the corresponding compound of formula I in which $R^1$ and $R^2$ are as defined herein, and $R^3$ and $R^4$ are hydrogen with about one molar equivalent of a trihalomethyl(lower)alkyl bromide, chloride or iodide in the same manner as described in the latter alkylation. Some compounds of formula I in which $R^3$ is trihalomethyl(lower)alkyl can be prepared by other methods. For instance, acylation of the compound of formula I in which $R^3$ and $R^4$ are hydrogen with a trihalomethyl(lower)alkylcarbonyl chloride or bromide, or an anhydride of a trihalomethyl(lower)alkylcarboxylic acid, in the same manner as described above for the preparation of the compounds of formula I in which $R^3$ is lower alkanoyl and reduction of the resulting amide with a complex metal hydride affords the corresponding compound of formula I in which $R^1$ and $R^2$ are as defined herein, $R^3$ is trihalomethyl(lower)alkyl having a methylene group adjacent the nitrogen, and $R^4$ is hydrogen. Preferably, the reduction is conducted with an excess of lithium aluminum hydride, as reducing agent, in an inert organic solvent, i.e. tetrahydrofuran, at about 30° to 80° C. for about 15 minutes to five hours.

The compounds of formula I in which $R^1$ and $R^2$ are as defined herein, $R^3$ is 2-, 3- or 4-pyridinyl(lower)alkyl, and $R^4$ is hydrogen can be prepared by converting the corresponding compound of formula I in which $R^1$ and $R^2$ are as defined herein, and $R^3$ and $R^4$ are hydrogen in the same manner as described above for the compounds of formula I in which $R^3$ is trihalomethyl(lower)alkyl. For instance, the compound of formula I in which $R^3$ and $R^4$ are hydrogen is alkylated with a 2-, 3- or 4-pyridinyl(lower)alkyl bromide, chloride or iodide; or acylated with a 2-, 3- or 4-pyridinyl(lower)alkylcarbonyl chloride or bromide, or an anhydride of a 2-, 3-, 4-pyridinyl(lower)alkylcarboxylic acid followed by reduction of the resulting amide.

Compounds of formula I in which $R^1$ and $R^2$ are as defined herein, $R^3$ is lower alkylaminocarbonyl or lower alkylaminothiocarbonyl, and $R^4$ is hydrogen can be prepared by reacting the corresponding compound of formula I in which $R^1$ and $R^2$ are as defined herein, and $R^3$ and $R^4$ are hydrogen with an excess of a lower alkyl isocyanate or lower alkyl isothiocyanate. Generally, the reaction is performed at 20° to 120° C. for 10 minutes to several days. An excess of the cyanate can act as the solvent for the reaction, or an inert organic solvent can be used, e.g. acetonitrile.

Alkylation of the compound of formula I in which $R^1$, $R^2$ and $R^3$ are as defined herein, and $R^4$ is hydrogen with a lower alkyl bromide, chloride or iodide, in the same manner as described above, gives the corresponding compound of formula I in which $R^1$, $R^2$ and $R^3$ are as defined herein, and $R^4$ is lower alkyl.

In another conversion, the compound of formula I in which $R^1$ is methoxy, and $R^2$, $R^3$ and $R^4$ are as defined herein can be demethylated with an excess of boron tribromide in an inert organic solvent, preferably methylene chloride, at about 0° to 50° C. for 5 to 30 hours to obtain the corresponding compound of formula I in which $R^1$ is hydroxy, and $R^2$, $R^3$ and $R^4$ are as defined herein. Preferred conditions include conducting the reaction at about 0° to 50° C. for five to 30 hours and the use of methylene chloride as an inert organic solvent.

The following examples illustrate further this invention.

EXAMPLE 1

Methyl 4-Chloro-2-hydroxybenzoate

A solution of 4-chloro-2-hydroxybenzoic acid (100 g, 0.58 mol), methanol (500 mL) and concentrated sulfuric acid (50 mL) was refluxed for 20 hr. Benzene (100 mL) was added and the solvent was slowly distilled off from the mixture until 300 mL of distillate was collected. The residue was taken up in diethyl ether, the aqueous phase was separated, the organic phase was washed with sodium bicarbonate solution, dried and evaporated to give 100 g of the title compound as an oil which crystallized on cooling; mp 27°–30° C., and IR (mineral oil) 3150, 1660 and 1600 cm$^{-1}$.

In the same manner, but replacing 4-chloro-2-hydroxybenzoic acid with an equivalent amount of 2-hydroxybenzoic acid, 5-bromo-2-hydroxybenzoic acid, 5-methyl-2-hydroxybenzoic acid, 5-chloro-2-hydroxybenzoic acid, 3-methyl-2-hydroxybenzoic acid, or 3-methoxy-2-hydroxybenzoic acid; the following esters were obtained, respectively: methyl 2-hydroxybenzoate; methyl 5-bromo-2-hydroxybenzoate, mp 59°–60° C.; methyl 2-hydroxy-5-methylbenzoate, NMR (CDCl$_3$) δ 2.25, 3.9, 7.2 and 10.5; methyl 5-chloro-2-methoxybenzoate, mp 44°–46° C.; methyl 2-hydroxy-3-methylbenzoate, NMR (CDCl$_3$) δ 2.25, 3.9, 7.25 and 10.9; and methyl 2-hydroxy-3-methoxybenzoate, mp 63°–65° C.

EXAMPLE 2

2-(2-Carbomethoxy-5-chlorophenoxy)acetonitrile (III: $R^1$=5-Cl)

A mixture of methyl 4-chloro-2-hydroxybenzoate (100 g, 0.53 mol, described in Example 1), chloroacetonitrile (53 g, 0.7 mol) and anhydrous potassium carbonate (110 g, 0.8 mol) in acetonitrile (750 mL) was stirred and refluxed for 5 hr. The solvent was evaporated and the residue was triturated with methylene chloride. The combined extracts were washed with 10% aqueous potassium carbonate solution and brine, dried and evaporated to give 113 g of crystalline product, m.p. 67°–69° C. The product was triturated with petroleum ether to give beige crystals of the title compound (75 g), mp 73°–76° C.

In the same manner, but replacing methyl 4-chloro-2-hydroxybenzoate with another ester described in Example 1, the following nitriles of formula III were obtained, respectively:

2-(2-carbomethoxyphenoxy)acetonitrile, mp 52°–54° C.;
2-(4-bromo-2-carbomethoxyphenoxy)acetonitrile, mp 85°–87° C.;
2-(2-carbomethoxy-4-methylphenoxy)acetonitrile, mp 63°–65° C.;
2-(2-carbomethoxy-4-chlorophenoxy)acetonitrile, mp 68°–69° C.;
2-(2-carbomethoxy-6-methylphenoxy)acetonitrile, mp 47°–48° C.; and
2-(2-carbomethoxy-6-methoxyphenoxy)acetonitrile, mp 74°–75° C. (dec.).

EXAMPLE 3

6-Chloro-3-hydroxybenzo[b]furan-2-carbonitrile (IV: $R^1$=6-Cl)

A mixture of 2-(2-carbomethoxy-5-chlorophenoxy)acetonitrile (22.6 g, 0.1 mol, described in Example 2) and sodium methoxide (0.2 mol, prepared from 4.6 g sodium metal and 50 mL dry methanol) in benzene (400 mL) was stirred and refluxed for 2 hr. After cooling, the precipitate was collected and dissolved in water. The solution was acidified with concentrated hydrochloric acid. The precipitate was extracted into diethyl ether and the solution was dried and evaporated. The solid residue was triturated with petroleum ether and gave 19.0 g of the title compound: mp ca 205° C., and NMR (DMSO-d$_6$) δ7.6 (3H,m), and 11.4 (1H, broad).

In the same manner, but replacing 2-(2-carbomethoxy-5-chlorophenoxy)acetonitrile with another nitrile of formula III described in Example 2, the following nitriles of formula IV were obtained, respectively:

3-hydroxybenzo[b]furan-2-carbonitrile, mp 143°–145° C.;
5-bromo-3-hydroxybenzo[b]furan-2-carbonitrile, IR (mineral oil) 3200 and 2220 cm$^{-1}$ and NMR (DMSO-d$_6$) δ7.7 (3H,m), 11.5 (1H, broad);
5-methyl-3-hydroxybenzo[b]furan-2-carbonitrile, mp 147°–151° C.;
5-chloro-3-hydroxybenzo[b]furan-2-carbonitrile;
7-methyl-3-hydroxybenzo[b]furan-2-carbonitrile, mp 165°–170° C.; and
7-methoxy-3-hydroxybenzo[b]furan-2-carbonitrile, mp 176°–178° C.

EXAMPLE 4

Ethyl 6-Chloro-3-hydroxybenzo[b]furan-2-carboximidate (V: $R^1$=6-Cl and Alk=Et)

To a solution of 6-chloro-3-hydroxybenzo[b]furan-2-carbonitrile (18 g, 93 mmol, described in Example 3) in dry ethanol (200 mL), dry hydrogen chloride gas was introduced for 1.5 hr while maintaining the reaction temperature at 10° to 15° C. After standing overnight at room temperature, the precipitate was collected and washed with diethyl ether to give 23 g of the hydrochloride salt of the title compound: mp 200°–205° C. (dec.); NMR (DMSO-d$_6$) δ1.45 (3H, t), 4.6 (2H, q), 7.35 (1H, dd), 7.7 (1H, d), 8.3 (1H, d), and 9.4 (3H, broad); IR (mineral oil): 3360, 3300, 2900, 2900 and 2400 cm$^{-1}$; and UV max (MeOH) 314 (ε=27290) and 239 nm (10180).

In the same manner, but replacing 6-chloro-3-hydroxybenzo[b]-furan-2-carbonitrile with another nitrile of formula IV described in Example 3, the following carboximidates of formula V were obtained, respectively:
ethyl 3-hydroxybenzo[b]furan-2-carboximidate hydrochloride, mp 154° C.;
ethyl 5-bromo-3-hydroxybenzo[b]furan-2-carboximidate hydrochloride, mp 220° C. (dec.) and NMR (DMSO-d$_6$) δ1.4, 4.5, 8.0 and 9.35;
ethyl 5-methyl-3-hydroxybenzo[b]furan-2-carboximidate hydrochloride, mp 160° C. (dec.);
ethyl 5-chloro-3-hydroxybenzo[b]furan-2-carboximidate hydrochloride, mp 273° C. (dec.);
ethyl 7-methyl-3-hydroxybenzo[b]furan-2-carboximidate hydrochloride, mp 148°–150° C.; and
ethyl 7-methoxy-3-hydroxybenzo[b]furan-2-carboximidate hydrochloride, mp 164°–167° C. (dec.).

EXAMPLE 5

6-Chloro-3-hydroxybenzo[b]furan-2-carboximidic Acid, 1-Methylhydrazide (IIa: $R^1$=6-Cl and $R^2$=Me)

A suspension of ethyl 6-chloro-3-hydroxybenzo[b]furan-2-carboximidate hydrochloride (23 g, 83.6 mmol, described in Example 4) in benzene (250 mL) was combined with methyl hydrazine (10 mL, ca 200 mmol) and the mixture was stirred and refluxed for 3 hr. The precipitate was collected and washed with diethyl ether to give 25 g of crude title product. A sample was recrystallized from isopropanol-diethyl ether to give light yellow crystals of the title compound: mp 240°–243° C. (dec.); NMR (DMSO-$d_6$) δ3.6 (3H, s), 5.15 (2H, s), 7.3 (3H, m), and 8.3 (2H, broad); and Anal. Calcd for $C_{10}H_{10}ClN_3O_2$: C, 50.11% H, 4.21% N, 17.53% and Found: C, 50.01% H, 4.19% N, 17.53%.

In the same manner, but replacing ethyl 6-chloro-3-hydroxybenzo-[b]furan-2-carboximidate with another carboximidate of formula V described in Example 4, the following hydrazides of formula IIa were obtained, respectively:

3-hydroxybenzo[b]furan-2-carboximidic acid, 1-methylhydrazide, mp 202°–203° C. (dec.);

5-bromo-3-hydroxybenzo[b]furan-2-carboximidic acid, 1-methylhydrazide, mp 197°–198° C. (dec.); IR (mineral oil) 3400, 3180, 3100, 2700 and 1600 cm$^{-1}$; and NMR (DMSO-$d_6$) δ2.6 (3H, s), 3.6 (3H, s) and 7.6 (3H, m);

5-methyl-3-hydroxybenzo[b]furan-2-carboximidic acid, 1-methylhydrazide, mp 149°–152° C.

5-chloro-3-hydroxybenzo[b]furan-2-carboximidic acid, 1-methylhydrazide, mp 188°–192° C.;

7-methyl-3-hydroxybenzo[b]furan-2-carboximidic acid, 1-methylhydrazide, mp 210°–215° C.; IR (mineral oil) 3390, 3240, 3130, 1670, 1625, 1575 and 1550 cm$^{-1}$; and NMR (DMSO-$d_6$) δ2.35 (3H, s), 3.6 (3H, s), 4.8 (2H, br), 7.2 (3H, m) and 8.35 (2H, br); and 7-methoxy-3-hydroxybenzo[b]furan-2-carboximidic acid, 1-methylhydrazide, mp 165°–167° C.; IR (mineral oil) 3420, 3130, 1665, 1625, 1560 and 1500 cm$^{-1}$; and NMR (DMSO-$d_6$) δ3.61 (3H, s), 3.92 (3H, s) and 7.60 (3H, m).

EXAMPLE 6

6-Chloro-2-methyl-2H-benzofuro[3,2-c]pyrazol-3-amine (Ia: $R^1$=6-Cl, $R^2$=Me and $R^3$ and $R^4$=H)

The crude 6-chloro-3-hydroxybenzo[b]furan-2-carboximidic acid, 1-methylhydrazide, (25 g, described in Example 5) was combined with polyphosphoric acid (250 g) and the mixture was stirred at 70°–80° C. for 4 hr. The hot mixture was poured into ice-water and the solution was made alkaline with 50% aqueous sodium hydroxide. The product was extracted several times with methylene chloride and the combined extracts were dried and evaporated. The crude product was triturated with diethyl ether to give the title compound (13 g): mp 210°–211° C.; IR (mineral oil) 3370, 3240 and 3120 cm$^{-1}$; UV max (MeOH) 227 nm (ε=15400), 253 (22100), shoulder 209 nm; NMR (DMSO-$d_6$) δ3.7 (3H, s), 5.4 (2H, s), and 7.5 (3H, m); and Anal. Calcd for $C_{10}H_8ClN_3O$: C, 54.19% H, 3.64%, N, 18.96% and Found: C, 53.91% H, 3.60% N, 18.90%.

In the same manner, but replacing 6-chloro-3-hydroxybenzo[b]furan-2-carboximidic acid, 1-methylhydrazide with another hydrazide of formula IIa described in Example 5, the following compounds of formula Ia were obtained, respectively:

2-methyl-2H-benzofuro[3,2-c]pyrazol-3-amine, mp 178°–179° C. (crystallized from isopropanol) and the hydrochloride salt thereof: mp 244°–246° C. (crystallized from methanol-diethyl ether); Anal. Calcd for $C_{10}H_9N_3O$·HCl: C, 53.69% H, 4.50% N, 18.78% and Found: C, 53.61% H, 4.53% N, 18.54%; NMR (DMSO-$d_6$) δ3.88 (3H, s), 7.65 (4H, m) and 8.05 (3H, s); and IR (mineral oil) 3260, 3130, 2640 and 1650 cm$^{-1}$;

7-bromo-2-methyl-2H-benzofuro[3,2-c]pyrazol-3-amine: mp 221° C. (dec.) (crystallized from isopropanol); IR (mineral oil) 3380, 3110 and 1650 cm$^{-1}$; UV max (MeOH) 306 nm (ε=4450), 277 (19600), 249 (22800); and NMR (DMSO-$d_6$) δ3.7 (3H, s), 7.7 (3H, m) and 5.4 (2H, br); and Anal. Calcd for $C_{10}H_8BrN_3O$: C, 45.13% H, 3.02% N, 15.79% and Found: C, 44.99% H, 3.07% N, 15.77%; 2,7-dimethyl-2H-benzofuro[3,2-c]pyrazol-3-amine: mp 164°–165° C. (crystallized from isopropanol); IR (mineral oil) 3380, 3260, 3160, 1650, 1620, 1525 and 1500 cm$^{-1}$; NMR (DMSO-$d_6$) δ2.4 (3H, s), 3.7 (3H, s), 5.3 (2H, s), and 7.25 (3H, m); and Anal. Calcd for $C_{11}H_{11}N_3O$: C, 65.67% H, 5.51% N, 20.88% and Found: C, 65.56% H, 5.56% N, 20.80%, and the hydrochloride salt of the latter compound: mp 227°–280° C. (dec.) (crystallized from methanol); and Anal. Calcd for $C_{11}H_{11}N_3O$·HCl: C, 55.58% H, 5.10% N, 17.68% and Found: C, 55.48% H, 5.10% N, 17.81%;

7-chloro-2-methyl-2H-benzofuro[3,2-c]pyrazol-3-amine: mp 214°–215° C. (crystallized from isopropanol); IR (mineral oil) 3380, 3100, 1650, 1620, 1600 and 1533 cm$^{-1}$; UV max (MeOH) 306 nm (ε=4610), 277 (12700), 249 (20240) and 211 (22080); NMR (DMSO-$d_6$) δ3.7 (3H, s), 5.45 (2H, s) and 7.5 (3H, m); and Anal. Calcd for $C_{10}H_8ClN_3O$: C, 65.67% H, 5.51% N, 20.88% and Found: C, 65.56% H, 5.56% N, 20.80%;

2,5-dimethyl-2H-benzofuro[3,2-c]pyrazol-3-amine, mp 156°–158° C., and the hydrochloride salt of the latter compound: mp 235°–245° C. (dec.) (crystallized from isopropanol-diethyl ether); IR (mineral oil) 3290, 3160, 2500, 1640, 1605, 1590, 1570, 1550 and 1500 cm$^{-1}$; UV max (MeOH) 299 nm (ε=8520), 274 (15900) and 259 (15550); NMR (DMSO-$d_6$) δ2.5 (3H, s), 3.85 (3H, s), 7.4 (3H, m) and 7.35 (5H, s); and Anal. Calcd for: $C_{11}H_{11}N_3O$·HCl: C, 55.58% H, 5.09% N, 17.68% and Found: C, 55.65% H, 5.06% N, 17.86%; and 5-methoxy-2-methyl-2H-benzofuro[3,2-c]pyrazol-3-amine: mp 186°–188° C. (crystallized from isopropanol); IR (mineral oil) 3390, 3300, 3170, 1660, 1585, 1535, and 1510 cm$^{-1}$; NMR (DMSO-$d_6$) δ3.7 (3H, s), 3.9 (3H, s), 5.11 (2H, s), and 7.1 (3H, m); and Anal. Calcd for $C_{11}H_{11}N_3O_2$: C, 60.82% H, 5.10% N, 19.35% and Found: C, 60.58% H, 5.08% N, 19.42% and the hydrochloride salt of the latter compound: mp 285°–287° C. (crystallized from methanol-diethyl ether); IR (mineral oil) 3280, 3140, 2600 and 1655 cm$^{-1}$; UV max (MeOH) 300 nm (ε=7470), 263 (16600), 231 (25100) and shoulder at ca. 307, 275, 258 and 266 nm: NMR (DMSO-$d_6$) δ3.95 (3H, s), 3.95 (3H, s), 7.3 (3H, m) and 7.95 (3H, s); and Anal. Calcd for $C_{11}H_{11}N_3O_2$·HCl: C, 52.07% H, 4.76% N, 16.56% and Found: C, 52.02% H, 4.71% N, 16.66%.

EXAMPLE 7

7-Bromo-N-butyl-2-methyl-2H-benzofuro[3,2-c]pyrazol-3-amine (Ia: $R^1$=7-Br, $R^2$=Me, $R^3$=H and $R^4$=Bu)

To a solution of 2-methyl-2H-benzofuro[3,2-c]pyrazol-3-amine (5.73 g, 21.53 mmol, described in Example 6) in dry tetrahydrofuran (THF, 200 mL) and pyridine (10 mL), butyryl chloride (4.6 mL, 42 mmol) was dropwise added at 5°–10° C. After 2 hr. the reaction mixture was taken to dryness in vacuo at room temperature (20°–22° C.) and the residue triturated with aqueous sodium bicarbonate solution. The product was collected, washed with water and dried to give N-(7-bromo-2-methyl-2H-benzofuro[3,2-c]pyrazol-3-yl)butyramide (5.30 g) as a light brown solid: mp 247°–248° C. (dec.); IR (mineral oil) 3250, 1675, 1655 and 1550 cm$^{-1}$; NMR (DMSO-d$_6$) δ0.95 (3H, t), 1.65 (2H, m), 2.4 (2H, m), 3.8 (3H, s), 7.7 (3H, m), and 10.0 (1H, s).

To a solution of the latter compound (3.32 g, 9.88 mmol) in dry THF (400 mL, freshly distilled), diborane (45 mL, 1 M in THF) was dropwise added at room temperature with stirring and the mixture was refluxed for 3 hr. After cooling, the solution was acidified by dropwise addition of 6 N aqueous HCl (100 mL) during 15 min at 0°–5° C. The mixture was heated and the THF was distilled off at atm. pressure. The residual aqueous phase was basified by addition of potassium hydroxide (KOH) pellets (cooling) and extracted with diethyl ether. The ether solution was dried and evaporated to give 10.9 g of an oil. The crude base was converted to the crystalline HCl-salt, the HCl salt was isolated and reconverted to the free base. The oily base was crystallized and triturated with hexane. The crystals were collected to give the title compound (2.66 g) as white crystals: mp 76°–78° C. (dec.); IR (CHCl$_3$) 3380, 1650, 1595 and 1535 cm$^{-1}$; UV max (MeOH) 312 nm (ε=4200), 280 (13000), 253 (22150); NMR (CDCl$_3$) δ1.0 (3H, t), 1.6 (4H, m), 3.35 (2H, m), 3.8 (3H, s) and 7.5 (3H, m); and Anal. Calcd for C$_{14}$H$_{16}$BrN$_3$O: C, 52.18% H, 5.00% N, 13.04% and Found: C, 51.89% H, 5.00% N, 13.04%.

EXAMPLE 8

N-(2,2,2-Trifluoroethyl)-2-methyl-2H-benzofuro[3,2-c]pyrazol-3-amine (Ia: $R^1$ and $R^3$=H, $R^2$=Me and $R^4$=CH$_2$CF$_3$)

A suspension of 2-methyl-2H-benzofuro[3,2-c]pyrazol-3-amine (2.41 g, 12.87 mmol, described in Example 6) in toluene (100 mL) was combined with trifluoroacetic anhydride (1.5 mL). The precipitate was collected, washed with toluene and dried to give a white solid (2.50 g), mp 201°–202° C. (dec.). Recrystallization of a sample from benzene gave N-(2-methyl-2H-benzofuro-[3,2-c]pyrazol-3-yl)trifluoroacetamide of mp 202°–203° C. (dec.); IR (mineral oil) 3270, 1715, 1175 and 1195 cm$^{-1}$; UV max (MeOH) 269 nm (ε=21300), shoulder 290, 280, 261, 236; NMR (DMSO-d$_6$) δ3.9 (3H, s), 7.5 (4H, m) and 11.1 (1H, s).

A solution of the latter compound (3.20 g, 11.30 mmol) in dry THF (30 mL, freshly distilled over lithium aluminum hydride) was added to a suspension of lithium aluminum hydride (1.9 g) in THF (30 mL) and the mixture was refluxed for 0.5 hr. Excess reagent was destroyed by slow addition of THF-H$_2$O with stirring and cooling. The mixture was filtered and the filtrate was dried and evaporated to dryness. Purification by chromatography on silica gel (eluant 5% MeOH—CHCl$_3$, v/v) and trituration of the eluate with petroleum-ether gave 2.1 g of a brown solid, mp 105°–113° C. Crystallization from methanol (charcoal) and from cyclohexane gave 1.20 g light yellow crystals mp 119°–120° C. A further crystallization from cyclohexane gave the title compound of mp 120°–121° C.; IR (CHCl$_3$) 3400, 3220 and 1160 cm$^{-1}$; UV max (MeOH) 249 nm (ε=5260), 270 (1540), 250 (16900) and 244 (16700); NMR (CDCl$_3$) δ3.85 (3H, s), 3.8 (2H, m), and 7.4 (4H, m); and Anal. Calcd for C$_{12}$H$_{10}$F$_3$N$_3$O: C, 53.53% H, 3.74% N, 15.60% and Found: C, 54.05% H, 3.74% N, 15.88%.

EXAMPLE 9

N-(6-Chloro-2-Methyl-2H-benzofuro[3,2-c]pyrazol-3-yl)acetamide (Ia: $R^1$=6-Cl, $R^2$=Me, $R^3$=H and $R^4$=COCH$_3$)

A mixture of 6-chloro-2-methyl-2H-benzofuro[3,2-c]pyrazol-3-amine (6.0 g, 27.1 mmol, described in Example 6) and acetic anhydride (60 mL) was stirred at room temperature for 2 hr. The precipitate was collected and washed with diethyl ether to give the title compound (7.0 g), mp 290°–300° C. Crystallization from ethanol gave title compound having mp 293°–298° C.: IR (mineral oil) 3220, 3170, 1665 and 1540 cm$^{-1}$; UV max (MeOH) 297 nm (ε=7755), 274 (22760) and 229 (21360); NMR (DMSO-d$_6$) δ2.13 (3H, s), 3.82 (3H, s), 7.33 (1H, 2d), 7.76 (1H, d) and 7.82 (1H, d); and Anal. Calcd for C$_{12}$H$_{10}$ClN$_3$O$_2$: C, 54.66% H, 3.82% N, 15.94% and Found: C, 54.52% H, 3.86% N, 15.86%.

EXAMPLE 10

N-(2-Methyl-2H-benzofuro[3,2-c]pyrazol-3-yl)-N$^1$-methylthiourea (Ia: $R^1$ and $R^3$=H, $R^2$=Me and $R^4$=CSNHCH$_3$ 2-Methyl-2H-benzofuro[3,2-c]pyrazol-3-amine (described in Example 6) was combined with excess methyl isothiocyanate (15 g) and the slurry was heated at reflux temperature (bath temp 150° C.) for 10 min. After cooling, diethyl ether was added. The precipitate was collected, washed with diethyl ether and dried to give 5.69 g off-white product, mp 241°–243° C. (dec.). Recrystallization from acetic acid (20 mL) gave 4.21 g white crystals (dried at 80° C., 3 days, vacuum) of the title compound: mp 246°–247° C.; IR (mineral oil) 3260, 3120 and 1425 cm$^{-1}$; UV max (MeOH) 269 nm (ε=25700), shoulder at 292, 282, 264, 247; NMR (DMSO-d$_6$) δ2.9 (3H, m), 3.8 (3H, s), 7.5 (4H, m), 8.05 (1H, br) and 9.4 (1H, s).

EXAMPLE 11

N-(2-Methyl-2H-benzofuro[3,2-c]pyrazol-3-yl)-N$^1$-methylurea (Ia: $R^1$ and $R^3$=H, $R^2$=Me and $R^4$=CONHCH$_3$)

A solution of 2-methyl-2H-benzofuro[3,2-c]pyrazol-3-amine (4.0 g, 21.37 mmol, described in Example 6) in acetonitrile (150 mL) was combined with excess methyl isocyanate (ca. 6 mL) and the mixture was stirred at room temperature for several days. The precipitate was collected, washed with acetonitrile and diethyl ether to give the title compound (4.54 g) as off-white crystals: mp ca. 290° C. (dec.); IR (mineral oil) 3310, 3250, 1635, 1655, 1580 and 1525 cm$^{-1}$; UV max (MeOH) 292 nm (ε=5656) and 269 (21000); NMR (DMSO-d$_6$) δ2.65 (3H, d), 3.8 (3H, s), 6.4 (1H, m), 7.3 (3H, m), 7.8 (1H, m)

and 8.35 (1H, s); and Anal. Calcd for $C_{12}H_{14}N_4O_2$: C, 59.01% H, 4.95% N, 22.94% and Found: C, 58.96% H, 5.00% N, 22.62%.

EXAMPLE 12

4-[(2-Methyl-2H-benzofuro[3,2-c]pyrazol-3-yl)amino]-2-butanone (Ia: $R^1$ and $R^3$=H, $R^2$=Me and $R^4$=2-oxobutyl)

A solution of 2-methyl-2H-benzofuro[3,2-c]pyrazol-3-amine (4.0 g, 21.37 mmol, described in Example 6) in ethanol (150 mL) was combined with excess methyl vinyl ketone (7 mL, ca. 80 mmol) and the solution was stirred for 1 day at room temperature. The solution was taken to dryness in vacuo at room temperature and a sticky solid (6 g) was obtained. Chromatography on silica gel and elution with 1% to 5% MeOH in $CHCl_3$ (v/v) gave 3.30 g of the title compound as beige crystals, mp. 136°–138° C. (dec.). Recrystallization from isopropanol (charcoal treatment) gave white crystals: mp 141°–142° C. (dec.); IR ($CHCl_3$) 3370 and 1710 $cm^{-1}$; UV max (MeOH) 298 nm ($\epsilon$=4790), 271 (15300) and 251 (18900); NMR ($CDCl_3$) $\delta$2.17 (3H, s), 2.8 (2H, t), 3.6 (2H, m), 3.77 (3H, s), and 7.5 (4H, m); and Anal. Calcd for $C_{14}H_{15}N_3O_2$: C, 65.35% H, 5.88% N, 16.33% and Found: C, 65.09% H, 5.85% N, 16.29%.

EXAMPLE 13

3-Amino-2-methyl-2H-benzofuro[3,2-c]pyrazol-5-ol (Ia; $R^1$=5-OH, $R^2$=Me, $R^3$ and $R^4$=H)

To a solution of 5-methoxy-2-methyl-2H-benzofuro[3,2-c]pyrazol-3-amine (2.84 g, 13.07 mmol, described in Example 6) in methylene chloride (180 mL), a large excess of boron tribromide (11 mL) was dropwise added during 15 min at 0°–5° C. The mixture was refluxed overnight and evaporated. The residue was taken up in ethanol-water (10:1, v/v, 100 mL), and the mixture was refluxed for 1 hr and evaporated. The residue was dissolved in water. The solution was filtered through diatomaceous earth to remove impurities then adjusted to pH 7.5 with aqueous sodium bicarbonate solution to give a precipitate. The precipitate was collected, washed with water and dried to give 1.69 g (64%) of a brownish solid, mp ca. 246°–258° C. The product was dissolved in methanol and the solution was treated with charcoal, filtered and evaporated. The residue was triturated in diethyl ether and collected to give 1.59 mp 282°–290° C. (dec.). The product was again dissolved in methanol and the solution was treated with charcoal, filtered and concentrated to a smaller volume during which crystallization occurred. The title compound was collected and washed with cold methanol to give 1.04 g of beige crystals: mp 287°–292° C. (dec.); IR (mineral oil) 3350 and 2900 $cm^-$; UV max (MeOH) 304 nm ($\epsilon$=6500), 265 (17210), 257 (18090) and 223 (22520); NMR (DMSO-$d_6$) $\delta$3.7 (3H, s), 5.3 (2H, s), 6.95 (3H, m) and 9.8 (1H, s); and Anal. Calcd for $C_{10}H_9$—$N_3O_2$: C, 59.10% H, 4.46% N, 20.68% and Found: C, 58.72% H, 4.47% N, 20.50%.

EXAMPLE 14

N-(2,5-Dimethyl-2H-benzofuro[3,2-c]pyrazol-3-yl)-2-pyridinemethaneamine (Ia; $R^1$=5—Me, $R^2$=Me, $R^3$=H and $R^4$=2-pyridinylmethyl)

A mixture of picolinic acid (1.23 g, 10 mmol) and thionyl chloride (5 mL, 70 mmol) in benzene (20 mL) was refluxed for 4 hr and evaporated to dryness. The acid chloride was dissolved in methylene chloride (20 mL) and the solution was dropwise added to a solution of 2,5-dimethyl-2H-benzofuro-[3,2-c]pyrazol-3-amine (1.0 g, 4.95 mmol, described in Example 6) in methylene chloride (20 mL) containing pyridine (2 mL). After stirring overnight at room temperature the precipitate was filtered off. The filtrate was washed with 5% aqueous hydrochloric acid, water, bicarbonate solution and again water, dried and evaporated to give a solid. The solid was triturated with diethyl ether to give 1.5 g product of mp 160°–165° C. Purification by chromatography (elution with 20% EtOAc—$CH_2Cl_2$, v/v) and trituration of the product with diethyl ether gave N-(2,5-dimethyl-2H-benzofuro[3,2-c]pyrazol-3-yl)-2-pyridinecarboxamide (1.0 g) mp 167°–168° C.: IR (mineral oil) 3350 and 1690 $cm^{-1}$; NMR ($CDCl_3$) $\delta$2.5 (3H, s), 4.0 (3H, s), 7.7 (7H, m) and 9.7 (1H, br); Anal. Calcd for $C_{17}H_{14}N_4O_2$: C, 66.65% H, 4.61% N, 18.29% and Found: C, 65.30% H, 4.41% N, 18.11%.

A solution of the latter compound (4.6 g, 15 mmol) in dry THF (50 mL) was dropwise added to a suspension of $LiAlH_4$ (4.6 g, 120 mmol) in THF (50 mL). The mixture was refluxed for 3 hr and the excess reagent was destroyed by addition of THF-water. The mixture was filtered and the filtrate was evaporated. A solution of the residue in methylene chloride was dried and evaporated to give 5.0 g of crude product. Chromatography on silica gel using 10% EtOH—EtOAc (v/v) as eluant gave the title compound which was directly converted by addition of HCl to the hydrochloride and crystallized from isopropanol-ethanol to give the hydrochloride salt of the title compound (1.5 g) was yellow crystals: mp 235°–240° C.; IR (mineral oil) 3330, 2650, 1645, 1620, 1580 and 1545 $cm^{-1}$; UV max (MeOH) 296 nm ($\epsilon$=6470) and 259 (21990); NMR (DMSO-$d_6$) $\delta$2.25 (3H, s), 3.85 (3H, s), 4.9 (2H, s), 5.35 (br) and 8.0 (7H, m); and Anal. Calcd for $C_{17}H_{16}N_4O \cdot HCl$: C, 55.90% H, 4.97% N, 15.34% and Found: C, 53.65% H, 4.99% N, 14.86%.

EXAMPLE 15

1-Methyl-1H-benzofuro[3,2-c]pyrazol-3-amine (Ib: $R^1$, $R^3$ and $R^4$=H and $R^2$=Me)

3-Hydroxybenzo[b]furo-2-carbonitrile (1.40 g, 8.8 mmol, described in Example 3) was dissolved with heating in benzene (50 mL) and methyl hydrazine (1 mL, ca. 19 mmol) was added. The solution was stirred and refluxed for 2 hr and evaporated to dryness. The pasty residue (ca. 2 g) was applied in chloroform solution to chromatography on neutral alumina. Elution with 2% MeOH in $CHCl_3$ (v/v) gave 3-hydroxybenzo[b]furan-2-carboximidic acid, 2-methylhydrazide (0.79 g): IR ($CHCl_3$) 3510, 3480, 3450, 3200, 1635 and 1595 $cm^{-1}$; and NMR ($CDCl_3$) $\delta$2.65 (3H, s), 5.7 (3H, broad), ca. 7.4 (1H, br), 7.2 (3H, m) and 7.75 (1H, d).

A mixture of the latter compound (730 mg, 3.56 mmol) and polyphosphoric acid (15 g) was heated with stirring at 100° C. (bath temp.) for 4–5 hr. The deep colored and clear solution was poured on ice-chips. The clear and cold solution was basified with 50% aqueous NaOH in presence of methylene chloride (70 mL) with stirring and cooling. The organic layer was separated and the aqueous phase was further extracted. The combined extracts were washed with water, dried ($K_2CO_3$) and taken to dryness to give 483 mg of dark colored semi-crystalline product. Chromatography on silica gel; elution with 5% MeOH—$CHCl_3$ (v/v) gave 435 mg of brown crystals. A sample was recrystallized from isopropanol to give orange-brown crystals of the title compound: mp 119°–120° C.; IR (mineral oil) 3400, 3330, 3260, 3180, 1620, 1580, 1555 and 1515 cm$^{-1}$; NMR (DMSO-d$_6$) δ3.8 (3H, s), 4.95 (2H, s) and 7.5 (4H, m); and Anal. Calcd for C$_{10}$H$_9$N$_3$O: C, 64.16% H, 4.85% N, 22.45% and Found: C, 63.85% H, 4.89% N, 22.23%.

EXAMPLE 16

1-(1-Methylethyl)-1H-benzofuro[3,2-c]pyrazol-3-amine (Ib: $R^1$, $R^3$ and $R^4$=H, and $R^2$=CH(Me)$_2$)

A suspension of ethyl 3-hydroxybenzo[b]furan-2-carboximidate hydrochloride (8.86 g 36.7 mmol, described in Example 4) in benzene (400 mL) was combined with freshly prepared acetone hydrazone (8.0 g, 110 mmol). A solution was formed then a precipitate occurred. The mixture was refluxed for 1.5 hr, additional acetone hydrazone (5.0 g, 69 mmol) was added and the solution was refluxed for 0.5 hr. The reaction mixture was filtered hot to remove the precipitate (discarded), the filtrate was evaporated to dryness and the residue was triturated with diethyl ether to give 6.2 g of 3-hydroxybenzo[b]furan-2-carboximidic acid, 2-(2-propanehydrazide), the mp of which, 218°–220° C. (dec.), remained constant on recrystallization from acetonitrile: IR (mineral oil) 3411, 3120, 1640, 1600, 1520, 1450, 1100 and 1190 cm$^{-1}$; NMR (DMSO-d$_6$) δ1.95 (3H, s), 2.00 (3H, s), 7.3 and 7.6 (4H, m), and ca. 7.6 (2H).

A solution of the latter compound (5.0 g, 21.62 mmol) in glacial acetic acid (400 mL) containing platinium oxide (500 mg) was hydrogenated for 12 hr. After removal of the catalyst, acetic acid was distilled off in vacuo and the crude oil (8.4 g) was purified by chromatography. Elution with chloroform containing increasing amounts of methanol (up to 10%) gave a crude solid, which after trituration with diethyl ether gave 2.4 g of 3-hydroxybenzo[b]furan-2-carboximidic acid, 2-(1-methylethyl hydrazide), mp 204° C. (dec.), 210°–212° C. (dec.) (from acetonitrile): IR (mineral oil) 3400, 3250, 3100, 1630, 1595, 1550 and 1510 cm$^{-1}$; NMR (DMSO-d$_6$) δ1.05 (6H, d), 3.05 (1H, m), ca. 7–7.6 (4H, m); and Anal. Calcd for C$_{12}$H$_{15}$N$_3$O$_2$: C, 61.78% H, 6.48% N, 18.02% and Found: C, 61.51% H, 6.50% N, 17.96%.

A mixture of the latter compound (2.4 g, 10.29 mmol) and polyphosphoric acid (24 g) was heated and stirred at 130° C. for 2 hr. After partial cooling, ice-chips were added followed by water. The resulting aqueous solution was basified (pH 10) with 50% aqueous sodium hydroxide and the mixture was extracted with chloroform. The organic solution was dried and evaporated to give 1.87 g of an oil of the title compound. The crude base was combined with 0.45 g of base from a different run and dissolved in ethanol. The solution was combined with a solution of one equivalent maleic acid in ethanol. Crystallization occurred on addition of diethyl ether to give 0.974 g of the maleate salt of the title compound, mp 101°–103° C. (In a different run, off-white crystals were obtained, mp 105°–106° C.) UV max (MeOH) 291 nm (ε=6150), and 248 (16500); NMR (DMSO-d$_6$) δ1.47 (6H, d), 4.60 (1H), 6.22 (2H, s), ca. 6.7 (3H, broad), and 7.2–8.3 (4H, m); Anal. Calcd for C$_{12}$H$_{13}$N$_3$O.C$_4$H$_4$O$_4$: C, 67.40% H, 4.90% N, 15.72% and Found: C, 66.53% H, 5.15% N, 15.74%.

EXAMPLE 17

N,2-Dimethyl-2H-benzofuro[3,2-c]pyrazol-3-amine (Ia: $R^1$ and $R^4$=H, and $R^2$ and $R^3$=Me)

A suspension of 2-methyl-2H-benzofuro[3,2-c]pyrazol-3-amine (3.8 g, 20 mmol, described in Example 6) in triethyl orthoformate (40 mL) was refluxed with stirring for 4 hr. The excess solvent was removed under vacuum and the residue was triturated with diethyl ether to give 4.5 g of N-ethoxymethylene-2-methyl-2H-benzofuro[3,2-c]pyrazol-3-amine, mp 120°–122° C., and NMR (CDCl$_3$) δ1.4 (3H, t), 3.95 (3H, s), 4.4 (2H, q), 7.5 (4H, m) and 8.5 (1H, s). The latter compound was suspended in ethanol (100 mL) and sodium borohydride (1 g, 26 mmol) was added in portions. The mixture was stirred at room temperature for 1 hr and at reflux temperature for 0.5 hr. The solution was evaporated to dryness and the residue was taken up in ethyl acetate. The solution was washed with water, dried and evaporated to dryness. Chromatography on silica gel and elution with 2% EtOH—CH$_2$Cl$_2$ (v/v) gave 2.5 g of crystalline product, mp 150°–156° C. The latter product was triturated with diethyl ether to obtain the title compound: mp 154°–156° C.; IR (mineral oil) 3190, 1640, 1600 and 1547 cm$^{-1}$; UV max (MeOH) 301 nm (ε=4820), 271 (14800), 251 (18900), 212 (20090) and shoulder 246; NMR (DMSO-d$_6$) δ2.97 (3H, d), 3.68 (3H, s), 5.51 (1H, q) and 7.0–8.0 (4H, m).

EXAMPLE 18

N,N,2-Trimethyl-2H-benzofuro[3,2-c]pyrazole-3-amine (Ia: $R^1$=H and $R^2$, $R^3$ and $R^4$=Me)

A mixture of acetic anhydride (200 mL) and 98% formic acid (10 mL) was heated at 50°–60° C. for 15 minutes. After cooling, 2-methyl-2H-benzofuro[3,2-c]pyrazol-3-amine (5.0 g, 27 mmol, described in Example 6) was added. After stirring overnight at room temperature, the mixture was poured on a mixture of ice and water and extracted with methylene chloride. The organic extract was dried and evaporated. The residue was chromatographed through silica gel using 5% EtOH—CH$_2$Cl$_2$ (v/v) and the eluates were evaporated. Trituration of the resulting residue with diethyl ether gave 3.0 g of N-(2-methyl-2H-benzofuro[3,2-c]pyrazol-3-yl)formamide: mp 184°–187° C.; IR (mineral oil) 3190 and 1670 cm$^{-1}$; UV max (MeOH) 269 nm (ε=21100), 222 (19500) and shoulder at 291 and 215; NMR (DMSO-d$_6$) δ3.85 (3H, s), 7.5 (4H, m), 8.4 (1H, s) and 10.4 (1H, br); and Anal. Calcd for C$_{11}$H$_9$N$_3$O$_2$: C, 61.39% H, 4.21% N, 19.53% and Found: C, 61.17% H, 4.27% N, 19.37%.

A solution of the latter compound (3.0 g, 14 mmol) in dry tetrahydrofuran (THF, 100 ml) was dropwise added under nitrogen to a stirred suspension of sodium hydride (50% in mineral oil, 2.7 g, 56 mmol) in THF (30 mL). After completion of the addition, the mixture was heated at 45° C. for 1 hr, and cooled to room temperature. Methyl iodide (7.95 g, 56 mmol) was added and the mixture was heated at 45° C. for 2 hr. With ice-water cooling, the excess sodium hydride was destroyed with water-THF. The organic solvent was evaporated and the aqueous phase was extracted with ethyl acetate. The combined extracts were treated with charcoal, dried and evaporated to dryness. The residue was chromatographed through silica gel using ethyl acetate eluant and the eluates were evaporated. The resulting residue (2.3 g) was triturated with diethyl ether to give N-methyl-N-(2-methyl-2H-benzofuro[3,2-c]pyrazol-3-yl)formamide: mp 135°–138° C.; IR (mineral oil) 1680 and 1645 cm$^{-1}$; and UV max (MeOH) 291 nm (ε=4800), 268 (31600), 213 (31600) and shoulder at 280.

To a solution of the latter formamide (2.3 g, 10 mmol) in THF (50 mL), diborane (25 mL, 1 M solution in THF) was added dropwise at 5°–10° C. under nitrogen. The mixture was stirred at room temperature overnight and acidified with 6 N aqueous hydrochloric acid. The THF was evaporated and the aqueous residue was made strongly alkaline with solid sodium hydroxide. The mixture was extracted with methylene chloride, and the organic extract was dried and evaporated. The residue was chromatographed through silica gel using diethyl ether to give an oil (0.6 g) of the title compound. The title compound was reacted with maleic acid and the resulting salt was crystallized from diethyl ether to obtain the maleate salt of the title compound: mp 81° C. (dec.); IR (mineral oil) 2500, 1715, 1620 and 1335 cm$^{-1}$; UV max (MeOH) 271 nm ($\epsilon=18100$), 261 (17500) and shoulder at 291 and 285; NMR (DMSO-d$_6$) $\delta$2.85 (6H, s), 3.8 (3H, s), 6.25 (2H, s), 7.5 (4H, m) and ca. 10 (2H, br); and Anal. Calcd for $C_{16}H_{17}N_3O_5$: C, 58.00% H, 5.17% N, 12.68% and Found: C, 57.88% H, 5.20% N, 12.43%.

We claim:

1. A compound of the formula

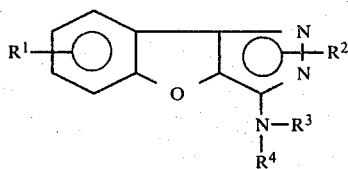

in which $R^1$ is hydrogen, halogen, lower alkyl, lower alkoxy, hydroxy or trifluoromethyl; $R^2$ represents one lower alkyl substituent on either of the adjacent nitrogen atoms; $R^3$ is hydrogen, lower alkyl, trihalomethyl(lower)alkyl; oxo(lower alkyl); lower alkanoyl; 2-, 3- or 4-pyridinyl(lower)alkyl; lower alkylaminocarbonyl or lower alkylaminothiocarbonyl; and $R^4$ is hydrogen or lower alkyl; or a therapeutically acceptable acid addition salt thereof.

2. The compound of claim 1 wherein $R^1$ is hydrogen, halogen, lower alkyl, lower alkoxy, or trifluoromethyl; $R^2$ represents one lower alkyl substituent on either of the adjacent nitrogen atoms; $R^3$ is hydrogen, lower alkyl, trifluoromethyl(lower)alkyl; oxo(lower)alkyl; or 2-pyridinyl(lower)alkyl; and $R^4$ is hydrogen or lowr alkyl; or a therapeutically acceptable acid addition salt thereof.

3. A compound of claim 1 having the formula

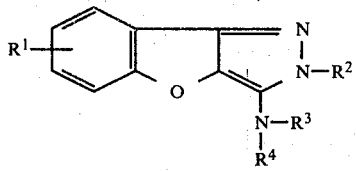

in which $R^1$ is hydrogen, halogen, lower alkyl, lower alkoxy, or trifluoromethyl; $R^2$ is lower alkyl; $R^3$ is hydrogen, lower alkyl, trifluoromethyl(lower)alkyl; or oxo(lower)alkyl; and $R^4$ is hydrogen or lower alkyl; or a therapeutically acceptable acid addition salt thereof.

4. The compound of claim 3 wherein $R^1$ is hydrogen, bromo, or lower alkyl; $R^2$ is methyl; $R^3$ is hydrogen, lower alkyl, trifluoromethyl(lower)alkyl or oxo(lower)alkyl; and $R^4$ is hydrogen, or a therapeutically acceptable acid addition salt thereof.

5. A compound of claim 1 having the formula

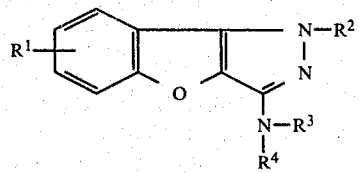

in which $R^1$ is hydrogen, halogen, lower alkyl, lower alkoxy, or trifluoromethyl; $R^2$ is lower alkyl; $R^3$ is hydrogen, lower alkyl, trifluoromethyl(lower)alkyl; or oxo(lower)alkyl; and $R^4$ is hydrogen or lower alkyl; or a therapeutically acceptable acid addition salt thereof.

6. The compound of claim 5 wherein $R^1$ is hydrogen, bromo, chloro, or lower alkyl; $R^2$ is methyl; $R^3$ is hydrogen, lower alkyl, trifluoromethyl(lower)alkyl or oxo(lower)alkyl; and $R^4$ is hydrogen, or a therapeutically acceptable acid addition salt thereof.

7. The compound of claim 1, which is 6-chloro-2-methyl-2H-benzofuro[3,2-c]pyrazol-3-amine.

8. The compound of claim 1, which is 2-methyl-2H-benzofuro[3,2-c]pyrazol-3-amine.

9. The hydrochloride salt of the compound of claim 8.

10. The compound of claim 1, which is 7-bromo-2-methyl-2H-benzofuro[3,2-c]pyrazol-3-amine.

11. The compound of claim 1, which is 2,7-dimethyl-2H-benzofuro[3,2-c]pyrazol-3-amine.

12. The compound of claim 1, which is 7-chloro-2-methyl-2H-benzofuro[3,2-c]pyrazol-3-amine.

13. The compound of claim 1, which is 2,5-dimethyl-2H-benzofuro[3,2-c]pyrazol-3-amine.

14. The compound of claim 1, which is 5-methoxy-2-methyl-2H-benzofuro[3,2-c]pyrazol-3-amine.

15. The compound of claim 1, which is 7-bromo-N-butyl-2-methyl-2H-benzofuro[3,2-c]pyrazol-3-amine.

16. The compound of claim 1, which is N-(2,2,2-trifluoromethyl)-2-methyl-2H-benzofuro[3,2-c]pyrazol-3-amine.

17. The compound of claim 1, which is N-(6-chloro-2-methyl-2H-benzofuro[3,2-c]pyrazol-3-yl)acetamide.

18. The compound of claim 1, which is N-(2-methyl-2H-benzofuro[3,2-c]pyrazol-3-yl)-$N^1$-methylthiourea.

19. The compound of claim 1, which is N-(2-methyl-2H-benzofuro[3,2-c]pyrazol-3-yl)-$N^1$-methylurea.

20. The compound of claim 1, which is 4-[(2-methyl-2H-benzofuro[3,2-c]pyrazol-3-yl)amino]-2-butanone.

21. The compound of claim 1, which is 3-amino-2-methyl-2H-benzofuro[3,2-c]pyrazol-5-ol.

22. The compound of claim 1, which is N-(2,5-dimethyl-2H-benzofuro[3,2-c]pyrazol-3-yl)-2-pyridinemethaneamine.

23. The compound of claim 1, which is N,2-dimethyl-2H-benzofuro[3,2-c]pyrazol-3-amine.

24. The compound of claim 1, which is 1-(1-methylethyl)-1H-benzofuro[3,2-c]pyrazol-3-amine.

25. The compound of claim 1, which is 1-methyl-1H-benzofuro[3,2-c]pyrazol-3-amine.

26. The compound of claim 1, which is N,N,2-trimethyl-2H-benzofuro[3,2-c]pyrazol-3-amine.

27. An analgesic composition, which comprises an effective amount of a compound of claim 1, or a therapeutically acceptable acid addition salt thereof, and a pharmaceutically acceptable carrier therefor.

28. A method of producing analgesia in a mammal, which comprises administering to the mammal an effective analgesic amount of a compound of claim 1, or a therapeutically acceptable acid addition salt thereof.

29. A method of producing analgesia in a mammal, which comprises administering to the mammal an effective analgesic amount of a compound of claim 1, or a therapeutically acceptable acid addition salt thereof, in combination with an effective amount of another analgesic agent selected from acetylsalicyclic acid, acetaminophen, aminopyrine, etodolac, codeine or morphine.

30. An analgesic composition comprising an effective amount of a compound of claim 1, or a therapeutically acceptable acid addition salt thereof, and an analgestic agent selected from acetylsalicylic acid, acetaminophen, etodolac, aminopyrine, codeine or morphine.

* * * * *